(12) United States Patent
Phan et al.

(10) Patent No.: US 11,607,154 B2
(45) Date of Patent: Mar. 21, 2023

(54) MAGNETO-LC RESONANCE TECHNOLOGY FOR REAL-TIME RESPIRATORY MOTION MONITORING

(71) Applicant: UNIVERSITY OF SOUTH FLORIDA, Tampa, FL (US)

(72) Inventors: Manh-Huong Phan, Tampa, FL (US); Ongard Thiabgoh, Tampa, FL (US); Tatiana Marie Eggers, Tampa, FL (US)

(73) Assignee: University of South Florida, Tampa, FL (US)

( * ) Notice: Subject to any disclaimer, the term of this patent is extended or adjusted under 35 U.S.C. 154(b) by 590 days.

(21) Appl. No.: 16/465,956

(22) PCT Filed: Dec. 21, 2017

(86) PCT No.: PCT/US2017/067860
§ 371 (c)(1),
(2) Date: May 31, 2019

(87) PCT Pub. No.: WO2018/119212
PCT Pub. Date: Jun. 28, 2018

(65) Prior Publication Data
US 2020/0029862 A1    Jan. 30, 2020

Related U.S. Application Data

(60) Provisional application No. 62/437,257, filed on Dec. 21, 2016.

(51) Int. Cl.
*A61B 5/113* (2006.01)
*C22C 19/00* (2006.01)
(Continued)

(52) U.S. Cl.
CPC ............ *A61B 5/113* (2013.01); *A61B 5/0816* (2013.01); *A61B 5/6823* (2013.01); *A61B 5/742* (2013.01);
(Continued)

(58) Field of Classification Search
CPC ..... A61B 5/113; A61B 5/0816; A61B 5/6823; A61B 5/742; A61B 2562/0223; C22C 19/00; G01D 5/2013
See application file for complete search history.

(56) References Cited

U.S. PATENT DOCUMENTS

2001/0026222 A1    10/2001  Canady
2007/0263699 A1    11/2007  Clothier
(Continued)

FOREIGN PATENT DOCUMENTS

ES              2277770 B1  *  6/2008  ............. G01D 5/142
WO    WO 2007/054602           5/2007
(Continued)

OTHER PUBLICATIONS

International Search Report and Written Opinion in International Application No. PCT/US2017/067860, dated Jun. 27, 2018, 18 pages.
International Preliminary Report on Patentability in International Application No. PCT/US2017/067860, dated Jul. 4, 2019, 15 pages.

*Primary Examiner* — Anthony M Liang
*Assistant Examiner* — Danny N Kang
(74) *Attorney, Agent, or Firm* — Fish & Richardson P.C.

(57) ABSTRACT

A non-contact respiratory monitoring system, method, and sensor are disclosed. The system includes a magnet and a sensor including a coil made of magnetic microwire. The magnetic microwire sensor coil is configured to detect motion of the magnet relative to the magnetic sensor coil. An alternating voltage across the magnetic microwire sensor coil is modified by a change in impedance of the magnetic (Continued)

microwire sensor coil caused by the change in the distance of the magnet from the magnetic microwire sensor coil. The non-contact respiratory monitoring method includes changing a distance of a magnet from a magnetic sensor coil. The sensor includes a coil composed of high quality melt-extracted amorphous microwire.

7 Claims, 10 Drawing Sheets

(51) Int. Cl.
    *G01D 5/20* (2006.01)
    *A61B 5/08* (2006.01)
    *A61B 5/00* (2006.01)

(52) U.S. Cl.
    CPC ........... *C22C 19/00* (2013.01); *G01D 5/2013* (2013.01); *A61B 2562/0223* (2013.01)

(56) References Cited

U.S. PATENT DOCUMENTS

| | | | |
|---|---|---|---|
| 2010/0087748 A1* | 4/2010 | Tobola | ............ A61B 5/113 600/529 |
| 2011/0105861 A1* | 5/2011 | Derchak | ............ G16H 20/30 600/301 |
| 2014/0228657 A1 | 8/2014 | Palley | |
| 2014/0343691 A1* | 11/2014 | Guillory | ............ A61F 2/72 623/25 |
| 2016/0228038 A1 | 8/2016 | Stone | |
| 2020/0029862 A1 | 1/2020 | Phan | |

FOREIGN PATENT DOCUMENTS

| | | | | |
|---|---|---|---|---|
| WO | WO-2007054602 A1 * | 5/2007 | ............ | G01D 5/142 |
| WO | WO 2015/087206 | 6/2015 | | |

* cited by examiner

MAGNETO-LC RESONANCE TECHNOLOGY FOR REAL-TIME RESPIRATORY MOTION MONITORING

CROSS-REFERENCE TO RELATED APPLICATIONS

This application is a National Phase Application under 35 U.S.C. § 371 of International Application No. PCT/US2017/067860, filed Dec. 21, 2017, which claims priority to U.S. Provisional Patent Application Ser. No. 62/437,257, filed on Dec. 21, 2016. The entire contents of the foregoing are hereby incorporated by reference.

TECHNICAL FIELD

Embodiments of the invention generally relate to methods and systems for non-contact respiratory monitoring. More particularly, certain embodiments are directed to a non-contact motion monitoring sensor comprising a magnetic microwire coil that magnetically couples to a magnet in motion.

BACKGROUND OF THE INVENTION

Respiration is an essential mechanism to sustain life in an organism by ensuring an adequate oxygen supply and carbon dioxide removal from the body. Therefore, monitoring the rate of respiration and its pattern can be used as crucial parameter to assess an individual's health or progression of an illness. In a normal state, the coordination of ventilation organs and the cardiovascular system perform a consistent respiratory rate and periodic rhythm or pattern. On the other hand, a change in rate or rhythmic pattern corresponding to an effort in breathing is found in abnormal states such as serious personal illnesses, obstructive sleep-apnea, cardiovascular disease, Cheyne-stroke, or heart failure. In addition, the respiratory patterns of many breathing disorders have been observed and documented for diagnostic and therapeutic purposes. Therefore, a reliable and accurate measurement of respiratory rate and pattern is crucial to ongoing efforts of diagnosing and monitoring illness in human patients.

Several methodologies, including contact and non-contact methods, are currently being used to monitor the respiration rate and pattern of patients. Of the non-contact methods, radar signal monitoring, optical based instruments, and thermal imaging analysis have been employed. While these non-contact methods are advantageous, for example in child respiration monitoring, sophisticated technology, high error and time consuming analysis is required for implementation. On the other hand, electrical impedance-based methods, known as impedance pneumography and respiratory inductance plethysmography (RIP), have been established and widely employed in contact-based respiratory rate monitoring. While these methods are more accurate and easier to use in respiration activity monitoring than the previously mentioned non-contact methods, they suffer from the downfalls of typical contact-based methods.

SUMMARY OF THE INVENTION

In some embodiments, a non-contact respiratory monitoring system comprises a magnet and a sensor. The sensor includes a coil made of magnetic microwire. The magnetic microwire sensor coil is configured to detect motion of the magnet relative to the magnetic sensor coil. The magnetic microwire sensor coil is oriented such that field lines emanating from the magnet are parallel to a cross-sectional area of the magnetic microwire sensor coil and the magnetic microwire sensor coil winding direction. The magnetic microwire sensor coil is positioned a distance from the magnet such that the magnetic microwire sensor coil is magnetically coupled to the magnet, and a change in the distance of the magnet from the magnetic microwire sensor coil causes a change of impedance in the magnetic microwire sensor coil. An alternating voltage across the magnetic microwire sensor coil is modified by a change in impedance of the magnetic microwire sensor coil caused by the change in the distance of the magnet from the magnetic microwire sensor coil.

In some embodiments, method for non-contact respiratory monitoring comprises changing a distance of a magnet from a magnetic sensor coil, where the magnetic sensor coil is made of magnetic microwire, configured to detect motion of the magnet relative to the magnetic microwire sensor coil, oriented such that field lines emanating from the magnet are parallel to a cross-sectional area of the magnetic microwire sensor coil and the magnetic microwire sensor coil winding direction, and positioned a distance from the magnet such that the magnetic microwire sensor coil is magnetically coupled to the magnet. The change in the distance of the magnet from the magnetic microwire sensor coil causes a change of impedance in the magnetic microwire sensor coil. An alternating voltage across the magnetic microwire sensor coil is modified by the change in impedance of the magnetic microwire sensor coil caused by the change in the distance of the magnet from the magnetic microwire sensor coil.

In some embodiments, a sensor comprises a coil comprised of high quality melt-extracted amorphous microwire with nominal composition $Co_{69.25}Fe_{4.25}Si_{13}B_{12.5}Nb_1$. The microwire has a diameter of about 60 µm. The coil includes 10 turns, is 7.0 mm in length, and has about a 3 mm internal diameter. The sensor is magnetically coupled to a magnet to detect a magnetic field of the magnet.

In some embodiments, a non-contact respiratory monitoring system comprises a magnet coupled to a patient's chest and a sensor comprising a 10-turn coil comprised of high quality melt-extracted amorphous microwire with nominal composition $Co_{69.25}Fe_{4.25}Si_{13}B_{12.5}Nb_1$. The sensor is positioned above the magnet and configured to detect a change in position of the patient's chest to determine a breathing pattern of the patient.

Other aspects of the invention will become apparent by consideration of the detailed description and accompanying drawings.

DETAILED DESCRIPTION

Figure 1A:
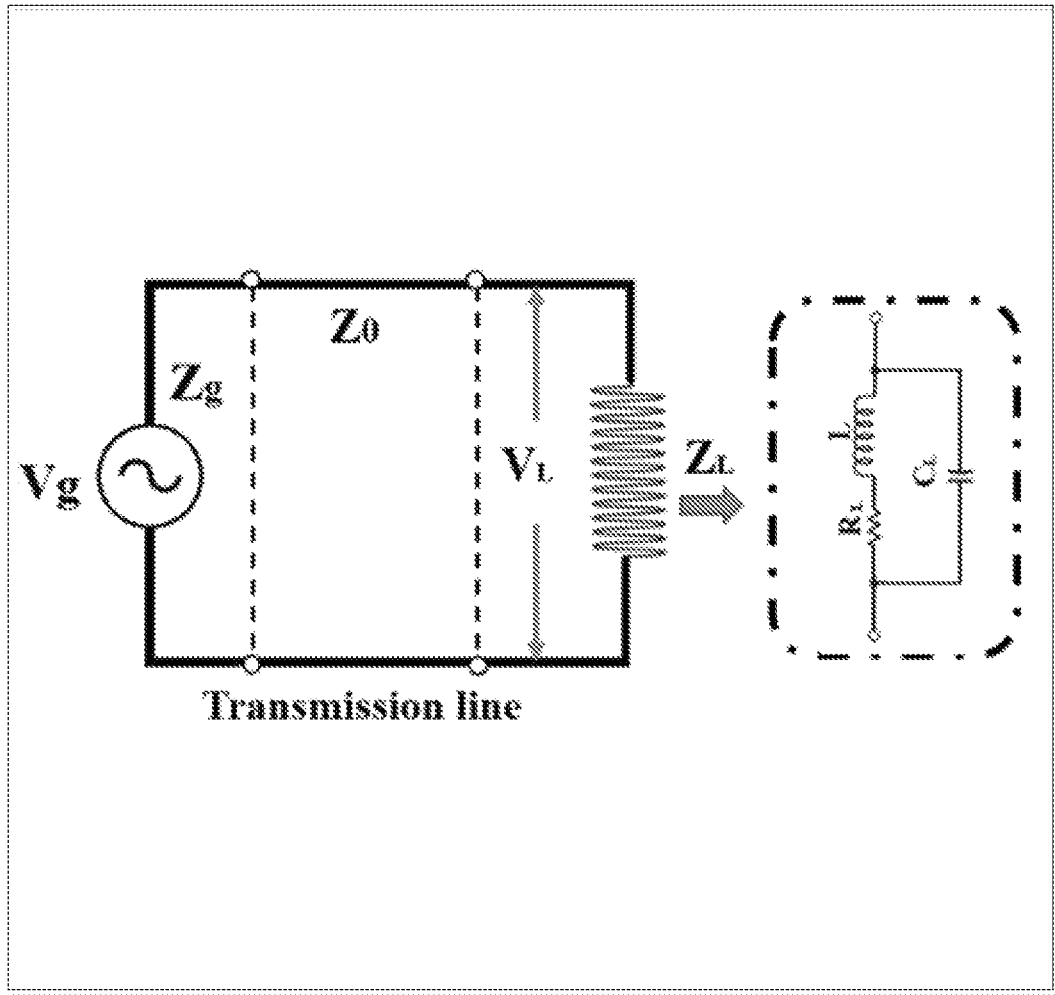
FIG. 1A illustrates an equivalent circuit of a MMC for a non-contact respiration rate monitoring device.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The working principle of a conventional magneto-inductive coil including induction of a voltage between the ends of conductors is widely used to detect certain magnetic fields. However, an inductive based device is reliable and accurate only for low working frequencies. The giant magneto-impedance (GMI) effect in a ferromagnetic conductor is useful for sensitive magnetic field sensing applications. In particular, cobalt-rich (Co-rich) amorphous magnetic microwires have high GMI ratios and magnetic field sensitivities. Both of these properties of magnetic microwires are suitable for long distance, non-contact sensing of small magnetic fields. Unlike copper wires used in inductive coils, Co-rich melt-extracted amorphous microwires demonstrate excellent magnetic field sensitivity for high working frequency measurements. The development of a small magnetic microwire coil (MMC) sensor is promising for a new type of real-time, non-contact respiratory monitor for monitoring a respiration process (i.e., breathing, or inhaling and exhaling of air).

Monitoring the rate of respiration and its pattern is crucial to assessing an individual's health or the progression of an illness. There is a pressing need for development of fast, reliable and cost-effective respiration monitors. A novel respiratory monitoring method and system based on a magnetic microwire coil (MMC) magneto-LC resonance sensor is presented. In one embodiment, a 3 mm diameter coil may be wound from a melt-extracted amorphous $Co_{69.25}Fe_{4.25}Si_{13}B_{12.5}Nb_1$ microwire. Unlike typical solenoids, the MMC coil is sensitive to small magnetic fields that are expressed as a significant change in impedance in the coil. This property is attributed to the high-frequency giant magneto-impedance (GMI) effect. For example, GMI effect may occur at operating frequencies of 1 MHz to 1 GHz. A method and system of an MMC sensor that detects a position-varying source having a small magnetic field, for example, approximately 0.01 to 20 Oe, for real-time respiratory monitoring of a human patient is described herein.

An MMC sensor application may be simulated for testing by mounting a small permanent magnet to a mechanical vibrator and vibrating the magnet at different frequencies, amplitudes, and waveforms at ~0.5-15 cm above the MMC (to act as the position varying source). Moreover, actual tests performed on a voluntary human subject demonstrate excellent performance of the MMC sensor. This newly developed MMC magneto-LC resonance method and system is highly promising for active respiratory motion monitoring and other biomedical field sensing applications.

The MMC sensor for the detection of small magnetic fields can be applied to real-time, non-contact respiratory monitoring. In non-contact MMC sensor respiratory monitoring, the MMC sensor does not touch the monitored subject, for example, the chest of a human subject. Described below are the operating principle of the MMC sensor, and the effective resistance (R), reactance (X), and impedance (Z) due to a small ambient magnetic field. Also provided are test results of simulated respiratory patterns with various changes in amplitudes, frequencies, and waveforms. Further provided are results of tests on a voluntary human subject, which illustrate the capabilities of non-contact and non-invasive real-time measurements by the MMC sensor for respiratory rate monitoring.

Moreover, a basic operating principle of the present MMC sensor is contrasted with contact-based impedance methods. In contact based impedance pneumography, two or four electrodes are attached to a patient's chest wall, and impedance across the probes is measured. Chest expansion and contraction change the impedance, thus recording a respiration pattern. In contact based respiratory inductance plethysmography (RIP), an elastic belt is embedded with an inductive coil and fastened around the chest or abdomen. The coil displacement caused by the chest expansion results in a change in inductance, thus a change in impedance. There are two major differences between the aforementioned contact based inductance methods and the presently described MMC sensor. First, in contrast with the inductance coil in RIP, which is made from copper-based materials (non-magnetic), the MMC sensor is constructed from an amorphous magnetic microwire (magnetic). This allows small external magnetic fields to significantly modify the inductance, hence the impedance. Use of a magnetic material allows the MMC sensor to be a non-contact impedance-inductance method since expansion or contraction of the coil is not required.

FIG. 1A illustrates an equivalent circuit of a MMC for a non-contact respiration rate monitoring device. Although the cause of an impedance change differs between the MMC and a copper coil, both can be understood through fundamental lumped-element circuit theory. The MMC coil is an inductor that creates a magnetic field when an electric current is flowing through it. Referring to FIG. 1A, a simplified model of a non-ideal inductor consists of a series inductance (L) and resistance ($R_L$) of the coil in parallel with a parasitic capacitance ($C_L$). The complex impedance ($Z_{coil}$) of the coil has two components, the first from the series combination of L and $R_L$ and the second from $C_L$ in parallel. By applying the definitions of inductive and capacitive reactance, the impedance of the coil can be expressed in terms of L, $R_L$, and $C_L$:

$$Z_{coil} = Z_{R_L} + Z_{C_L} \quad (1)$$

$$Z_{coil} = \frac{1}{\dfrac{1}{R_L + i\omega L} + \dfrac{1}{-i/\omega C_L}} \quad (2)$$

$$Z_{coil} = \frac{R_L + i\omega[L(1 + \omega^2 L C_L) - C_L R_L^2]}{(1 - \omega^2 L C_L)^2 + (\omega C_L R_L)^2}, \quad (3)$$

where $Z_{coil}$ is the coil impedance, $\omega$ is the angular frequency, and i is the imaginary unit. For a small loop of wire with high conductivity, the $R_L$ would be very small and negligible. The coil impedance for the highly conducting limitation recovers:

$$Z_{coil} \cong \frac{\omega L}{1 - \omega^2 L C_L}. \quad (4)$$

When the $\omega^2 L C_L$ term approaches one, the coil impedance becomes very large and exhibits a self-resonance phenomenon. At this moment, very little current flows into the loops which is known as anti-resonance. The resonance frequency is given as $$f_0 = \frac{1}{2\pi \sqrt{L C_L}}, \quad (5)$$

where $f_0$ is the resonance frequency. At high operating frequencies, $R_L$, L, and $C_L$ have significant frequency dependencies and the Z should be measured with an impedance or network analyzer devices.

In some embodiments, an MMC 110 sensor may be constructed from a high quality melt-extracted amorphous microwire with nominal composition $Co_{69.25}Fe_{4.25}Si_{13}B_{12.5}Nb_1$. The diameter of the microwire may be ~20-100 µm. In one embodiment, the diameter of the microwire is ~60 µm. The fabrication details and material characterization of the microwires can be found elsewhere. In one embodiment, the magnetic coil has 10 turns, is 7.0 mm in length, has a 3 mm internal diameter, and is wound around a quartz tube. In other embodiments, the magnetic coil may include 5-20 turns, have a length of 5-10 mm, an internal diameter of 2-5 mm, and be wound around a quartz or plastic tube, for example.

Figure 1B:
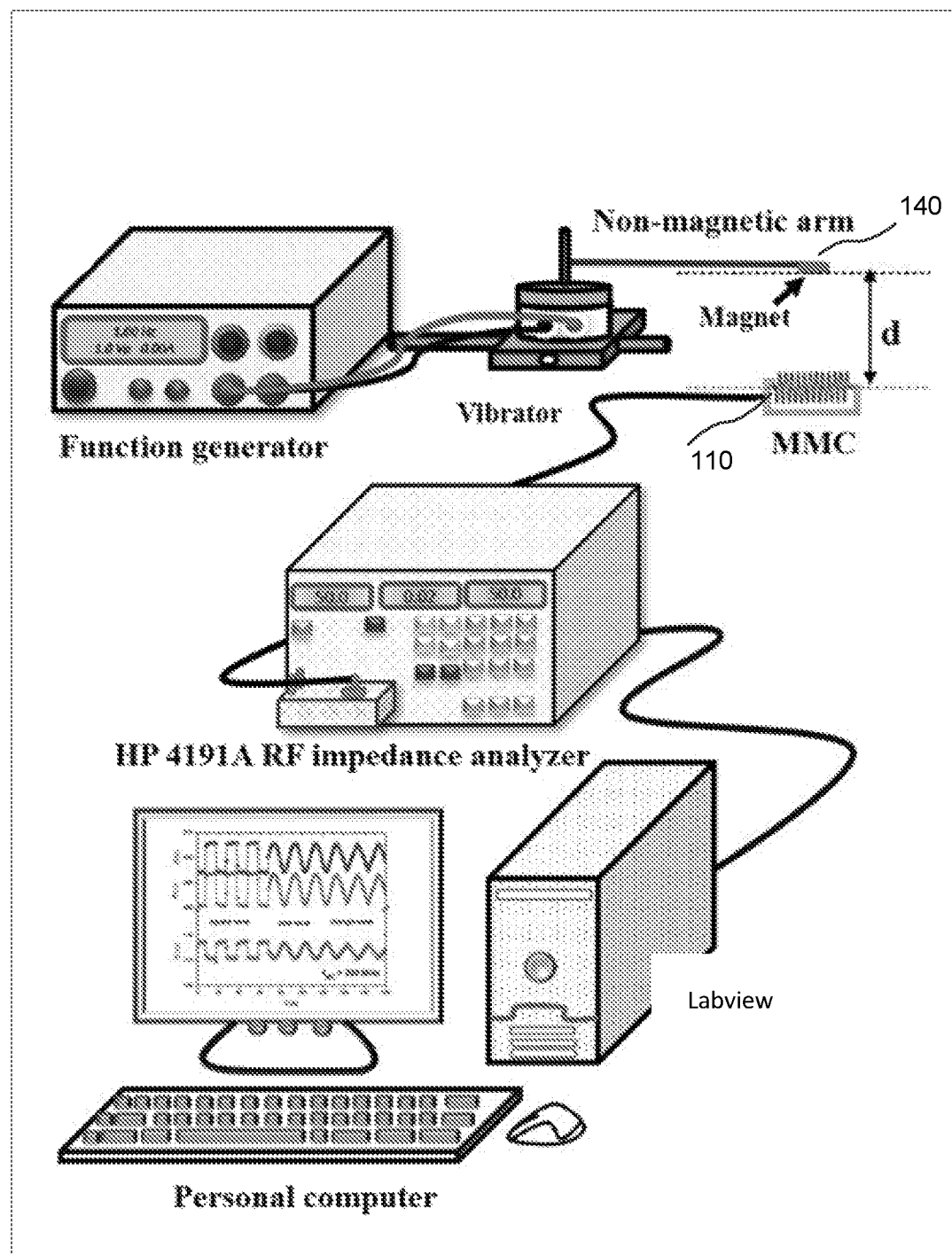
FIG. 1B illustrates an experimental set up for a magnetic coil sensor of a MMC for a non-contact respiration rate monitoring device.

FIG. 1B illustrates an experimental set up for a magnetic coil sensor of a MMC for a non-contact respiration rate monitoring device. FIG. 1B includes a MMC 110. The experimental MMC 110 sensor was constructed from a high quality melt-extracted amorphous microwire with nominal composition $Co_{69.25}Fe_{4.25}Si_3B_{12.5}Nb_1$. A conventional inductive coil was also constructed for a comparative study with a commercial copper wire with 86.36 µm diameter.

The frequency dependence of the effective impedance (Z), resistance (R), and reactance (X) of the MMC 110 was measured over high frequency range (1 MHz-1 GHz) using an HP Agilent 4191A RF impedance analyzer interfaced with a LABVIEW program. The MMC 110 was mounted onto a board with copper cladding on the opposite side. A coaxial cable of about 50 cm length was connected to the board via an SMA port, which was connected to the HP Agilent 4191A RF impedance analyzer represented in FIG. 1B. The HP 4191A was calibrated at the end of the 50 cm SMA cable using a typical open, short, load (50 Ω) standards. A frequency sweeping measurement of R, X, and Z was performed for the MMC 110 and, for comparison, a non-magnetic copper coil. To introduce a source of a small magnetic field, a cylindrical 8 mm×4 mm Neodymium magnet was fixed to a non-magnetic arm attached to a mechanical vibrator. The average distance between the coils and the permanent magnet was 3.0 cm, which can be extended up to 15 cm. The magnetic field was determined to be ~10 Oe at the center of the MMC 110 by a Gauss meter.

A function generator was activated to drive the mechanical vibrator and create a position-varying source of a small magnetic field. This portion of the setup was built to simulate the chest movements of a human patient during respiration. The mechanical vibrator was driven at various frequencies of $f_{vib}$~0.02-0.2 Hz, and vibrational amplitudes ranging from 0.12-1.51 mm representing different respiration rates and depths, respectively. In order to investigate the sensing discrimination, three different waveforms (square, sine, triangle wave) were used.

Figure 1C:
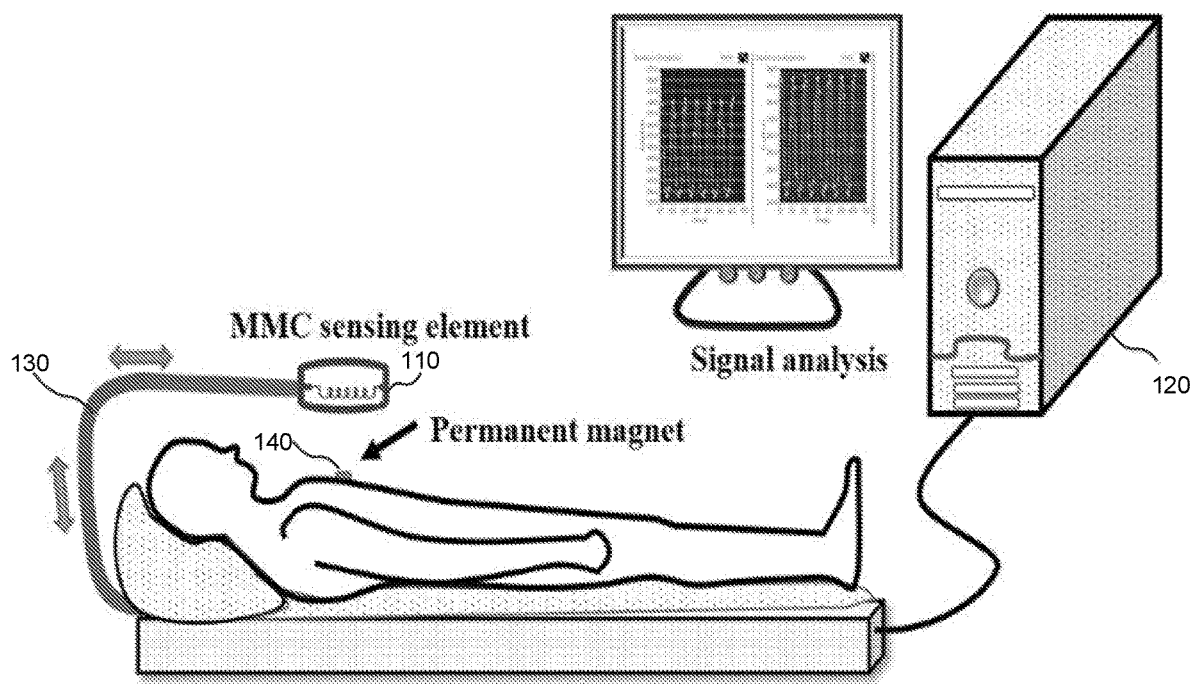
FIG. 1C illustrates an example of operation of a MMC for a non-contact respiration rate monitoring device.

FIG. 1C illustrates an example operation of a MMC for a non-contact respiration rate monitoring device. FIG. 1C includes the MMC 110 sensor, a magnet 140, a computer processing system 120, and a communication link 130. FIG. 1C represents an application of the MMC 110 for respiratory rate monitoring of a subject. To test the practical applicability of the MMC 110 sensor, respiratory rate monitoring was performed with a voluntary, healthy human subject (male, 38 years old, and 65 kg). In this trial, the human subject was lying down on a smooth table in a sleeping-like position. A small cylindrical magnet 140 was attached onto the human subject's abdomen using an adhesive tape. The MMC 110 sensing element, which experiences a small magnetic field ~4 Oe, was directly positioned 5 cm above the magnet 140. The human subject was instructed to perform normal and controlled breathing during the measurement. A MMC 110 sensed signal was acquired and recorded via the experimental setup for signal analysis as represented in FIG. 1C.

As a result of the experiment, the impedance of the MMC 110 and, for comparison, the copper coil was measured over the frequency range (1 MHz-1 GHz) in the absence and presence of an external magnetic field aligned perpendicularly to the coil axis.

Figure 2:
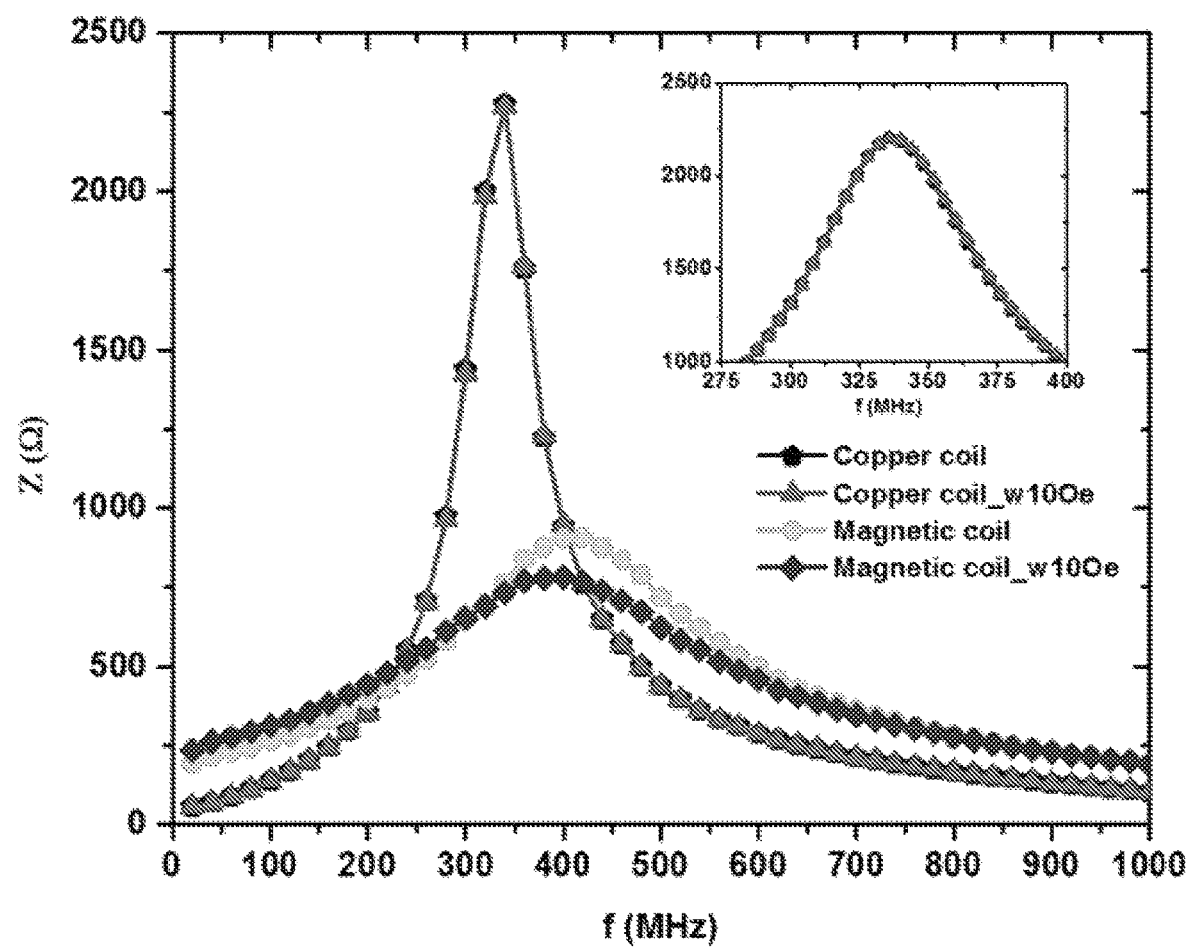
FIG. 2 is a graphical illustration of frequency dependence of the effective impedance (Z) of a copper coil and MMC (10 turns, D=3 mm) before and after introducing H-field ~10 Oe. Inset shows an enlarged region around the resonance frequency of the copper coil.

FIG. 2 is a graphical representation of frequency dependence of effective impedance (Z) of a copper coil and an MMC 110 (having 10 turns, and internal diameter D=3 mm) before and after introducing an H-field of approximately 10 Oe. The inset of FIG. 2 represents an enlarged region around the resonance frequency of the copper coil. FIG. 2 shows that the self-resonance frequency of the copper coil and the MMC 110 without an external magnetic field occurs around 340 MHz, and 440 MHz, respectively. The frequency shift between these two impedance maxima occurs due to different $R_L$ and $C_L$ properties of the coil materials. The magnitude of $Z_{Cu\ coil}$ is much larger than $Z_{MMC}$ due to the high conductivity approximation given in Eq. 4. The negligible $R_L$ of the copper coil allows the denominator of Eq. 4 to reach a smaller value, hence a more pronounced peak in the impedance, when an excitation frequency approaches the self-resonance frequency, $f_{ac}$~340 MHz. Unlike the copper coil, the MMC has a higher resistivity, thus a lower magnitude of the impedance at its self-resonance frequency, since $R_L$ cannot be neglected.

The more interesting features of FIG. 2, that is, more applicable to sensor development, are the significant peak shift and magnitude change of $Z_{MMC}$ with the application of a small magnetic field. The obtained measurement ensures the advantages of the MMC magneto-LC resonance sensor for small field detection, for example, a few mOe. It can be seen from FIG. 2, the significant increase in the Z after introducing the small magnetic field to the MMC coil was observed at working frequencies less than 340 MHz. On the other hand, the measured Z noticeably decreases from the initial value at higher frequencies. Therefore, the working frequency certainly plays an essential role for a magnetic field sensing design. The magnitude change and peak location shift, owing to the interaction of the external magnetic field and the magnetic microwire, are highly promising characteristics for the development of a respiration rate monitor using a magnetic marker, such as a small permanent magnet 140, on the patient body. To further explore the sensing capability of the MMC, the following sections will be devoted to examining the potential of frequencies around (and including) the self-resonance peak location of $Z_{MMC}$ as the driving frequency for the sensor.

Figure 3A:
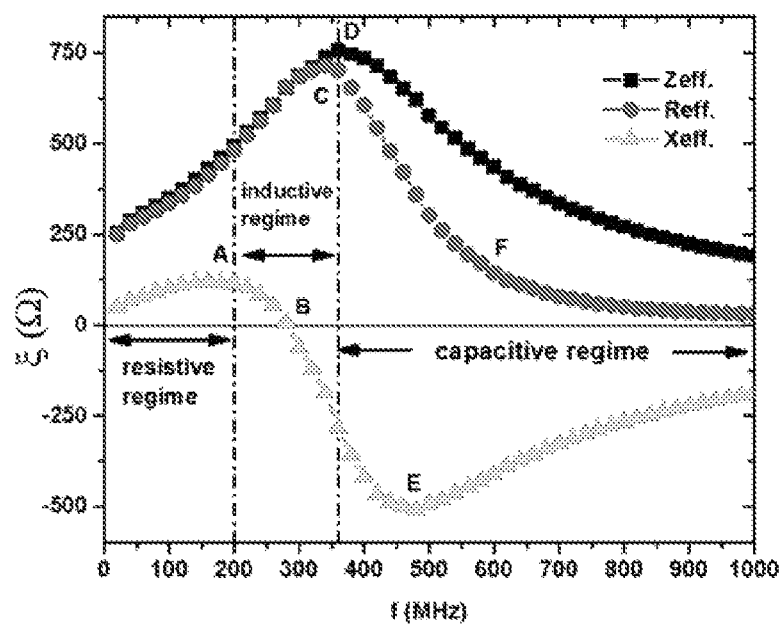
FIG. 3A is a graphical illustration of frequency dependence of the effective impedance (Z), resistance (R), and reactance (X) of the MMC coil with no magnetic field present.

FIG. 3A is a graphical illustration of frequency dependence of the effective impedance (Z), resistance (R), and reactance (X) of the MMC coil with no magnetic field present. As mentioned previously, the constructed coils are composed of the inductance, L, and the parasitic elements $R_L$ and $C_L$. The frequency dependent circuit characteristics for the coil can be split into three regimes: resistive, inductive, and capacitive, as defined in FIG. 3A. Taking a closer look into the resistive ($f_{ac} \leq 200$ MHz) and inductive regimes ($200 < f_{ac} \leq 360$ MHz), the measured R contributes to Z more than X does. However, R and X both significantly contribute to Z in the capacitive regime for the higher frequency range ($f_{ac} > 360$ MHz).

Figure 3B:
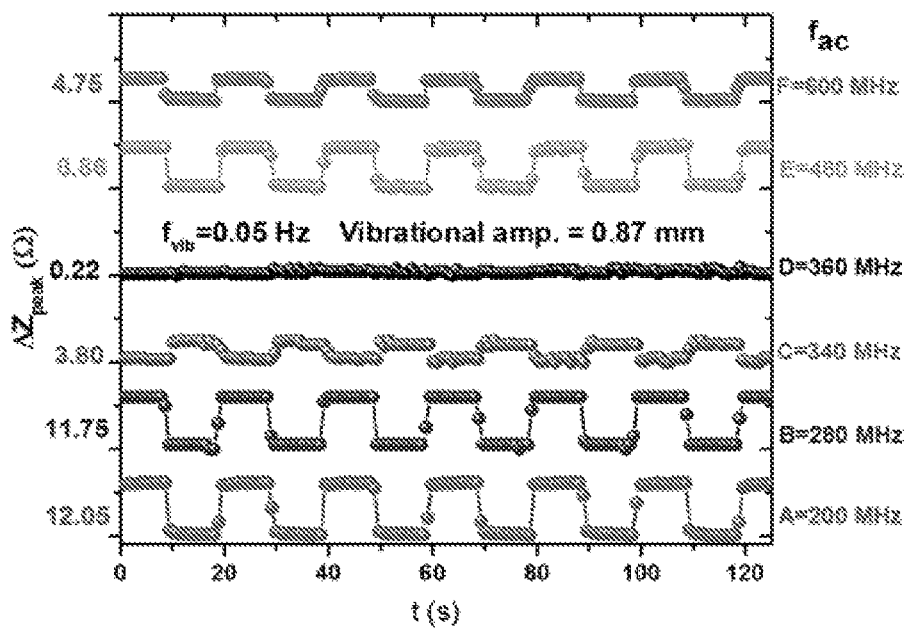
FIG. 3B is a graphical illustration of time dependence of Z of the MMC coil under the influence of a small permanent magnet vibrating at 0.05 Hz a displacement of 0.87 mm at different working frequencies.

FIG. 3B is a graphical illustration of time dependence of Z of the MMC coil under the influence of a small permanent magnet 140 vibrating at 0.05 Hz and a displacement of 0.87 mm, at different working frequencies. To gain more insight into the impedance response owing to a position-varying magnetic field, the time dependence of the impedance was measured at several working frequencies, as seen in FIG. 3B: f=200 MHz (A), 280 MHz (B), 320 MHz (C), 340 MHz (D), 480 MHz (E), and 600 MHz (F). The working frequencies were chosen where R, X, and Z exhibit a maximum: $f_{ac}$~200 MHz (A), 340 MHz (C), and 360 MHz (D) MHz, respectively. FIG. 3B shows the change in the effective impedance ($\Delta Z_{peak}$) detected from the position-varying permanent magnet 140 at a distance d~3 cm away from the MMC 110. The mechanical vibrator was operated at frequency $f_{vib}$=0.05 Hz with a displacement of ~0.78 mm. It can be seen from FIG. 3B that the large changes in Z occur at $f_{ac}$~200, 280, and 480 MHz which are located on the resistive, inductive, and capacitive regimes, respectively. Therefore, any of these points are suitable for the field sensing operation. Conversely, as shown in FIG. 3B, there is no significant change in Z observed at the LC-resonance frequency $f_{ac}$~360 MHz. At LC-resonance, there is a superposition of opposite flowing currents and as a consequence there is no potential difference across the coil and the coil behaves similar to an open circuit. As a result, the change in the impedance of the MMC is less pronounced at the resonance frequency.

Figure 4A:
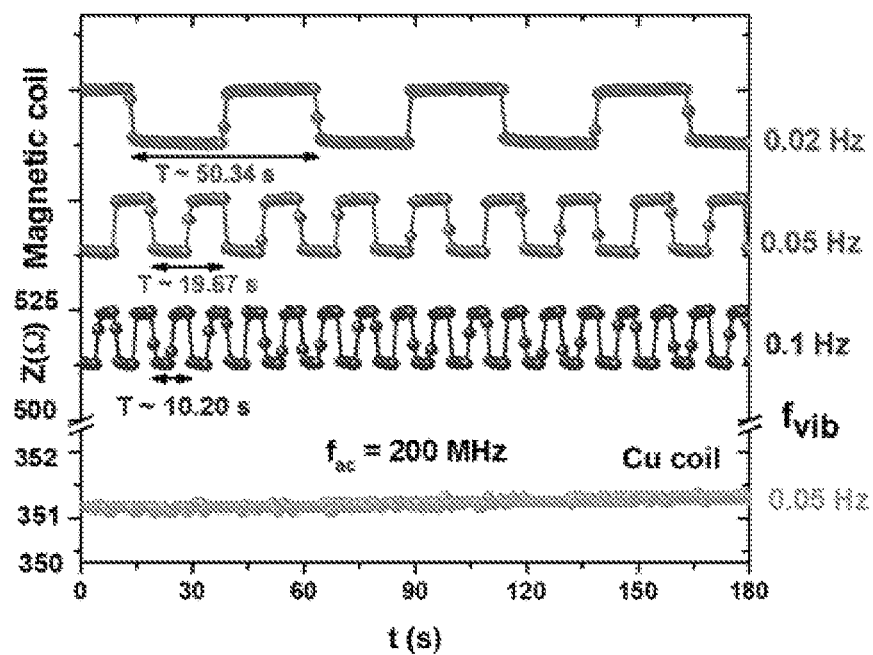
FIG. 4A is a graphical illustration of the time dependence of the change in impedance (Z) of the MMC due to the position-varying magnet at different $f_{vib}$. The impedance change of the copper coil under the vibrating magnet at $f_{vib}$ is shown for comparison.

FIG. 4A is a graphical representation of the time dependence of the change in impedance (Z) of the MMC 110 due to the position-varying magnet 140 at different $f_{vib}$. The impedance change of the copper coil under the vibrating magnet 140 at $f_{vib}$ is shown for comparison. The coil sensing reliability was scrutinized for the working frequency $f_{ac}$~200 MHz. FIG. 4A shows the change in impedance resulting from a square waveform applied to the mechanical vibrator and attached magnet 140 at $f_{vib}$=0.1, 0.05, and 0.02 Hz and amplitude ~0.87 mm. As seen from the period extracted from the impedance change in FIG. 4A, the original oscillatory pattern applied to the mechanical vibrator and attached magnet 140 is recovered. Unsurprisingly, the copper coil shows no significant change in Z over time since there is no interaction with a small magnetic field. In general, conventional (non-magnetic) solenoids are sensitive only to the ambient field perpendicular to the cross-sectional coil area since the only way a voltage can be induced in this coil is by Faraday's law of induction. For all cases presented in this work, the majority of the field lines emanating from the permanent magnet 140 are parallel to the cross-sectional area of the coils, which is parallel to the coil winding direction. For example, the cross-sectional area of the coil is an area bound by the circumference of a loop of the coil. In this configuration, the magnetic microwire of the MMC 110 exhibits a significant and sensitive response to small magnetic fields due its magneto-impedance properties.

Figure 4B:
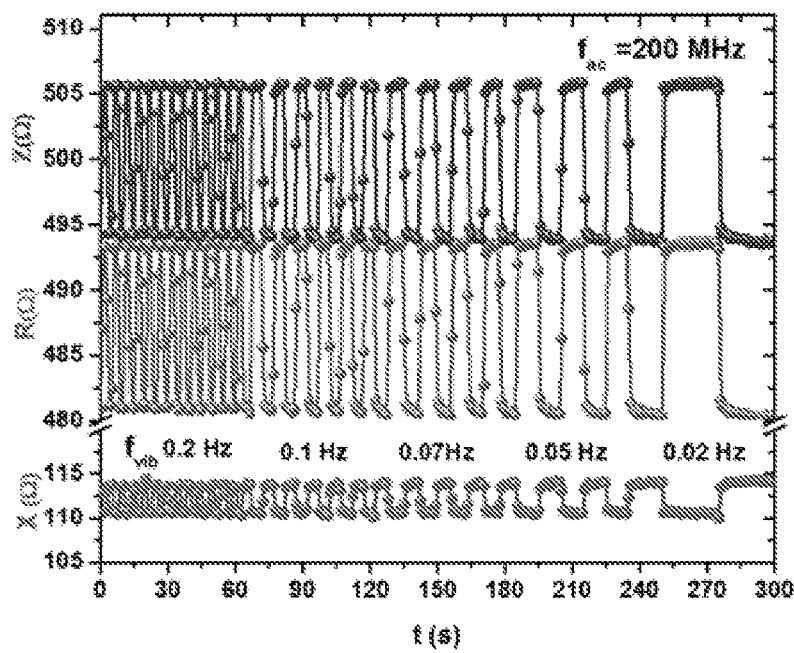
FIG. 4B is a graphical illustration of the time dependence of R, X, and Z of the MMC coil at different vibrational frequencies.

FIG. 4B is a graphical representation of the time dependence of R, X, and Z of the MMC coil 110 at different vibrational frequencies. FIG. 4B shows the R and X components of Z at different $f_{vib}$. At an excitation frequency of $f_{ac}$=200 MHz, the R component contributes most to Z as expected in the resistive regime. What can be noticed in this figure is that monitoring either R or X of the MMC coil 110 is promising for a magnetic field sensor. As mentioned previously, the large change in resistance and reactance due to the small position-varying magnetic field is a direct result of the giant magneto-impedance effect.

By applying a small permanent magnet 140 to the patient's chest wall, small movements of varying frequency can be detected by the MMC coil 110. To simulate this effect, several different driving frequencies (0.02 to 0.2 Hz) have been applied to the function generator to simulate different breathing rates as seen in FIG. 4B. It has been found that during a normal rest state, adult breathing occurs at a consistent rate of 12-20 breaths per minute or 0.2-0.3 Hz, while a rapid breathing rate of ~40 breaths per minute or 0.7 Hz has been found in an excited state. Moreover, apnea events from patients with respiratory abnormalities can be easily detected as a flat line in the impedance response. Overall, the impedance responses illustrated in FIG. 4B demonstrate great promise for breathing state detection.

Figure 5A:
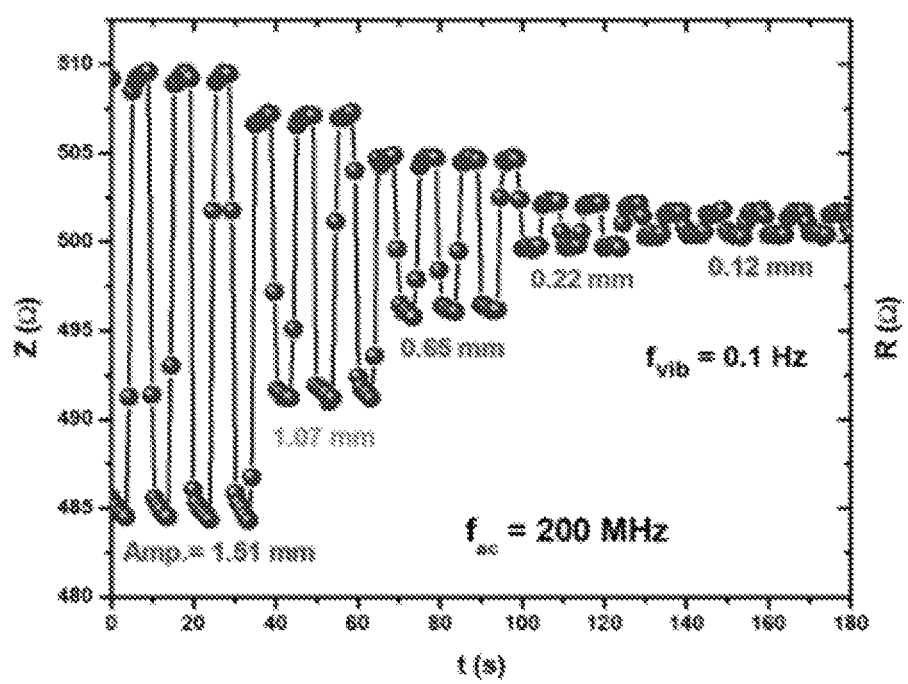
FIG. 5A is a graphical illustration of the time dependence of the measured impedance (Z) from the vibrational magnet with different amplitudes.
Figure 5B:
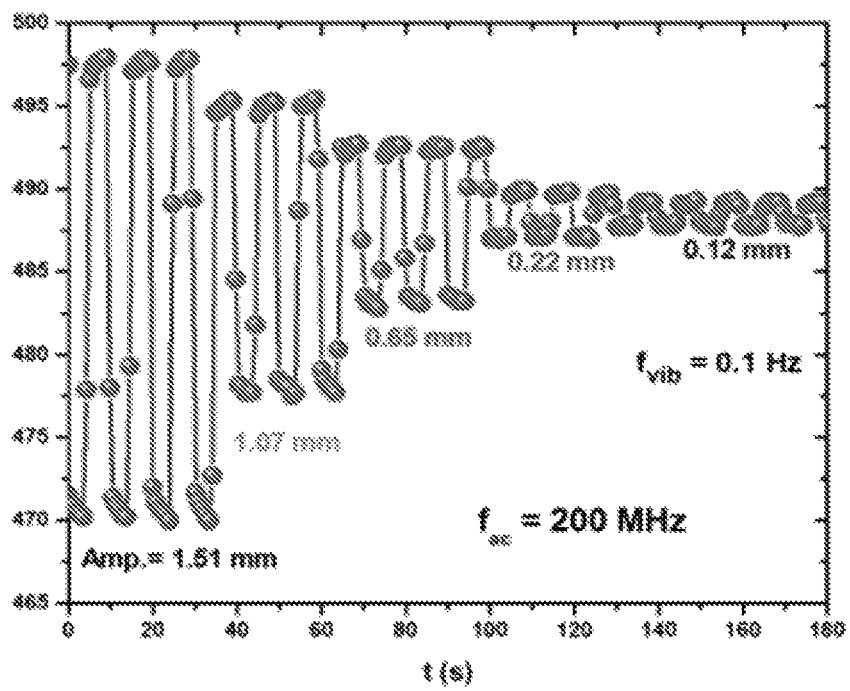
FIG. 5B is a graphical illustration of the time dependence of the measured resistance (R) from the vibrational magnet with different amplitudes.
Figure 5C:
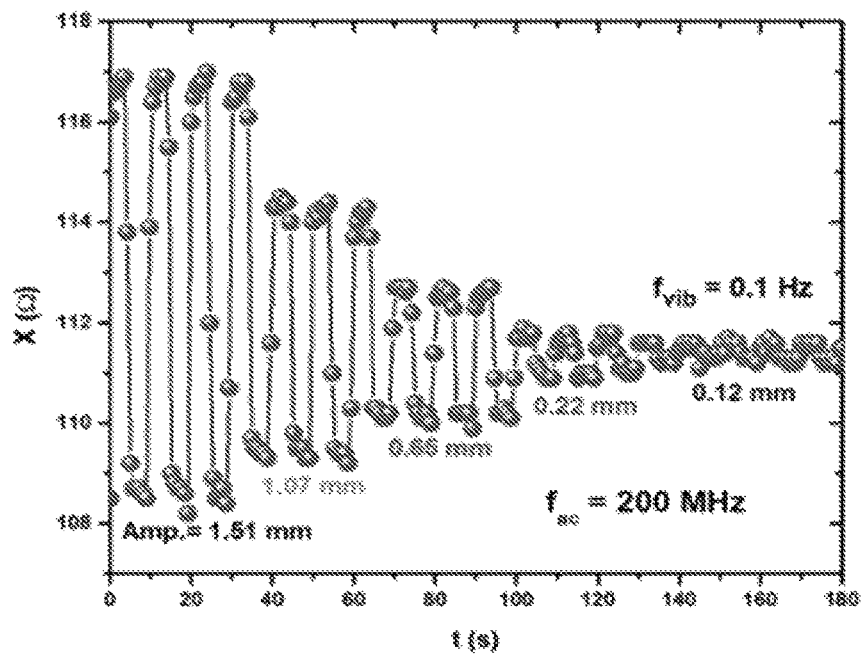
FIG. 5C is a graphical illustration of the time dependence of the measured reactance (X) from the vibrational magnet with different amplitudes.

FIG. 5A is a graphical representation of the time dependence of measured impedance (Z) from the vibrational magnet 140 with different amplitudes. FIG. 5B is a graphical representation of the time dependence of measured resistance (R) from the vibrational magnet 140 with different amplitudes. FIG. 5C is a graphical representation of the time dependence of measured reactance (X) from the vibrational magnet 140 with different amplitudes. In order to demonstrate the ability of the MMC coil 110 to detect a depth of breathing, the vibration amplitude of the function generator with various vibrational magnitudes was performed. Referring to FIGS. 5A-5C, the R, X, and Z plots show marked responses to small changes in vibration amplitudes, 1.15, 1.07, 0.65, 0.22, and 0.12 mm over time for the working frequency ~200 MHz. The R values contribute to the Z more than X does. The measured Z increases when the magnetic marker 140 moves from the lowest to the highest position, and exhibits a similar feature as the R value. Unlike the R and Z responses, however, X shows a reverse response. As mentioned previously, this is due to the impedance responses of the ferromagnetic microwires at high stimulating frequencies of the motion of the magnet 140. This magnetic field sensitive response can be used for real-time respiratory monitoring. Furthermore, it has been demonstrated that sleep-disordered breathing patterns in Cheyne-stoke, sleep apnea, and chronic heart failure patients have similar features to those represented in FIG. 5. Moreover, the respiratory rate measuring from the abdomen and chest wall movements of a human subject exhibits similar characteristics. Therefore, the incorporated distinct sensing characteristics of the MMC coil 110, shown in FIGS. 4A, 4B, 5A, 5B and 5C, are detected and recognized for respiratory rate and patterns.

Figure 6:
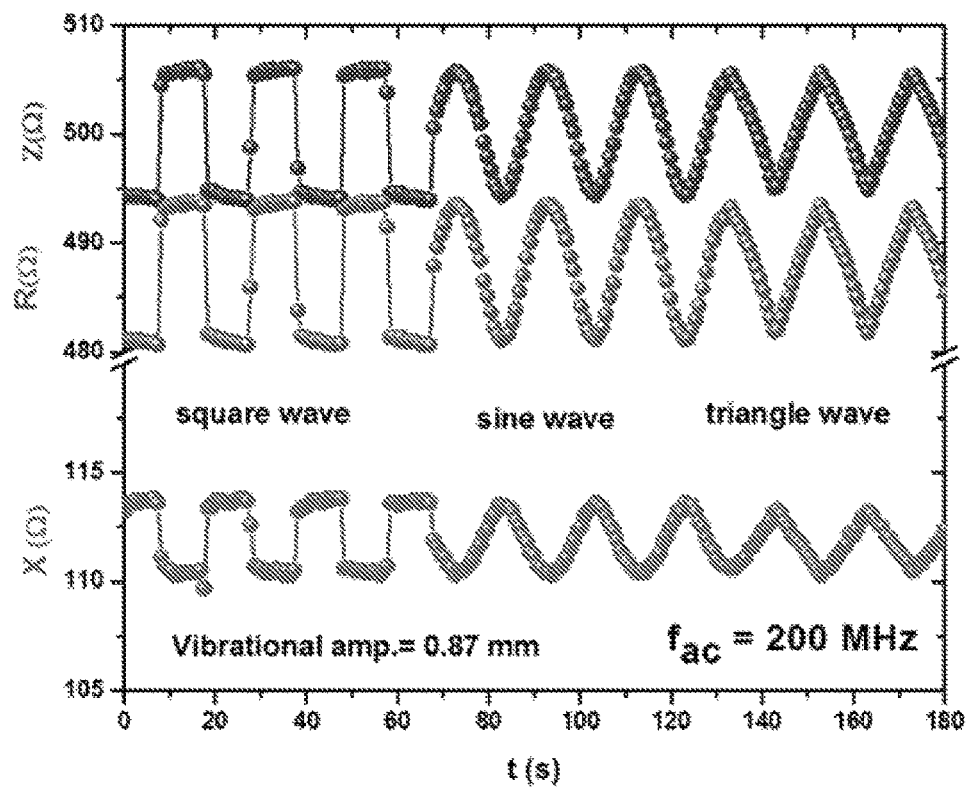
FIG. 6 is a graphical illustration of the time dependence of the measured impedance (Z) from the vibrational magnet with different types of waveforms.

FIG. 6 is a graphical representation of the time dependence of measured impedance (Z) from the vibrational magnet 140 when vibrated with different types of waveforms. Discrimination of input magnetic field signals generated from various oscillatory patterns such as square, sine, and triangle waves was investigated. A response from the input-modulated signals is shown in FIG. 6. The retrieved amplitude and $f_{vib}$ are consistent and reliable over the time measurement. Similar trends are seen relative to the preceding responses. Responses of the MMC 110 to the external magnetic field for the R, and Z are comparable in magnitudes, but the measured X has reverse change attributed to the magnetic field as expected. As mentioned earlier, common respiratory patterns, for example, sinusoidal wave type, triangular wave, square-like shape, varying periods, increasing depth etc. have been recognized and may be observable via the MMC 110. The sensing characteristics demonstrated in FIG. 6 of the MMC 110 are suitable for real-time respiratory measurement.

Figure 7A:
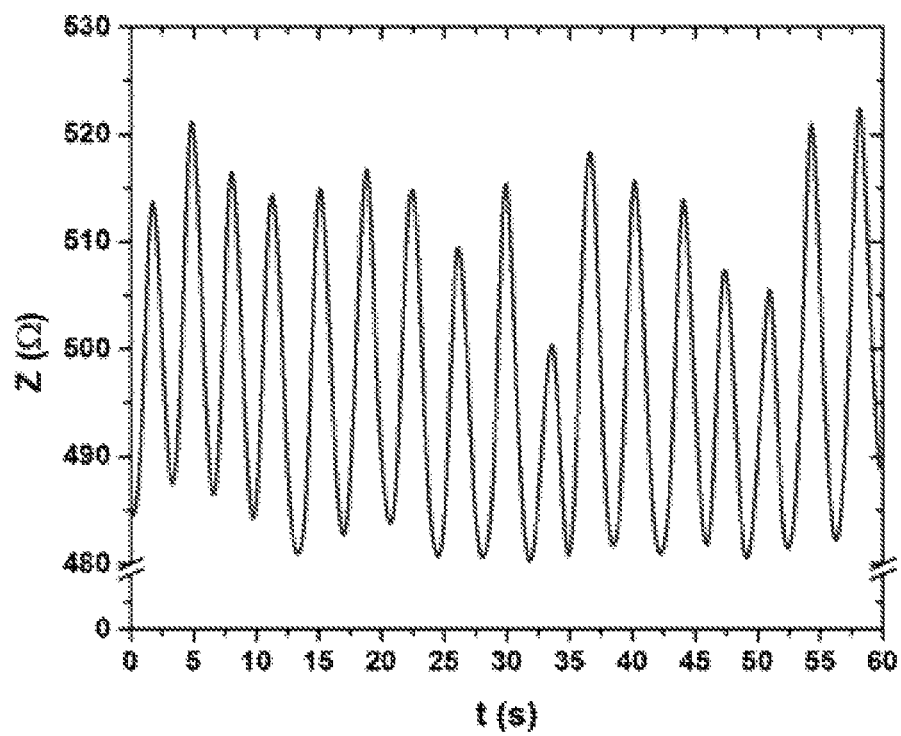
FIG. 7A is a graphical illustration of breathing patterns (impedance vs. time) of a healthy man in normal breathing.
Figure 7B:
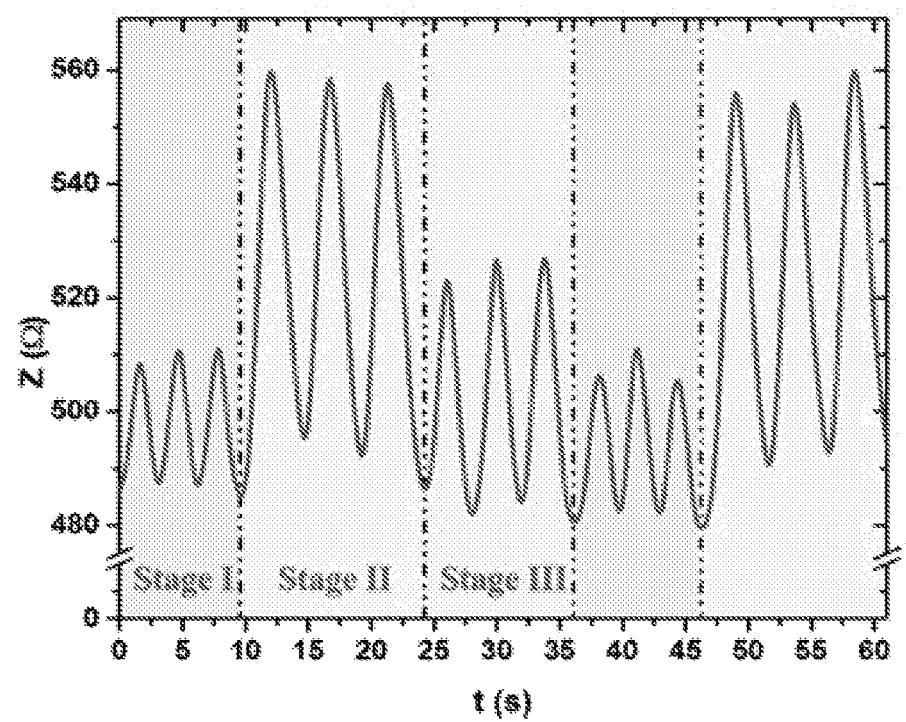
FIG. 7B is a graphical illustration of breathing patterns (impedance vs. time) of a healthy man in the controlled breathing (three different amplitudes of breathing) modes.

FIG. 7A is a graphical representation of breathing patterns, indicated by impedance vs. time, of a healthy man in normal breathing mode. FIG. 7B is a graphical representation of breathing patterns, indicated by impedance vs. time, of a healthy man in the controlled breathing (three different amplitudes of breathing) modes. Practical applicability of the MMC 110 magneto-LC resonance technology for active respiratory monitoring is provided. FIGS. 7A and 7B represent signals obtained from the trial sessions described above, using a working frequency of 200 MHz. The acquired signals shown in FIGS. 7A and 7B display precise, real-time respiratory patterns of a healthy man, who voluntarily participated in the test. Referring to FIG. 7A, normal to controlled breathing modes are shown. In the recorded pattern, the controlled breathing rate can be determined to be 17 cycles per 60 seconds, or 17 breaths per minute. The recorded normal breathing corresponds to the first three peaks (first 10 seconds, Stage I). The human subject was then instructed to perform a deeper inhale per breath (aimed at increasing the amplitude of breathing), which corresponds to the next three peaks (between 10 and 25 seconds, Stage II). The human subject was then instructed to slightly reduce his breathing amplitude which corresponded to the next three lower peaks (between 25 and 35 seconds, Stage III). Finally, the human subject was instructed to return to Stage I (between 35 and 45 seconds). The discrimination of a breathing pattern was further illustrated in FIG. 7B. All these results demonstrate the capability of the MMC 110 magneto-LC resonance technology for active respiratory motion monitoring of a human patient.

An MMC 110 sensor made from soft ferromagnetic amorphous microwire has been demonstrated for small magnetic field sensing. The reliable and sensitive responses in measured R, X, and Z of the MMC 110 to an applied external magnetic field were investigated. A change in the impedance was observed when the MMC 110 experienced a small magnetic field with various amplitudes, frequencies, and waveform-types of oscillations. The MI response to a small oscillatory magnet 140, which virtually simulated physiological movements corresponding to human-respiratory activities, was observed. The actual tests on the voluntary human subject were performed, demonstrating the excellent performance of the sensor. This newly developed MMC magneto-LC resonance technology is much more sensitive compared to conventional magnetic sensors and therefore very promising for active, non-contact respiratory monitoring of a human patient and for other biomedical field sensing applications.

Figure 8:
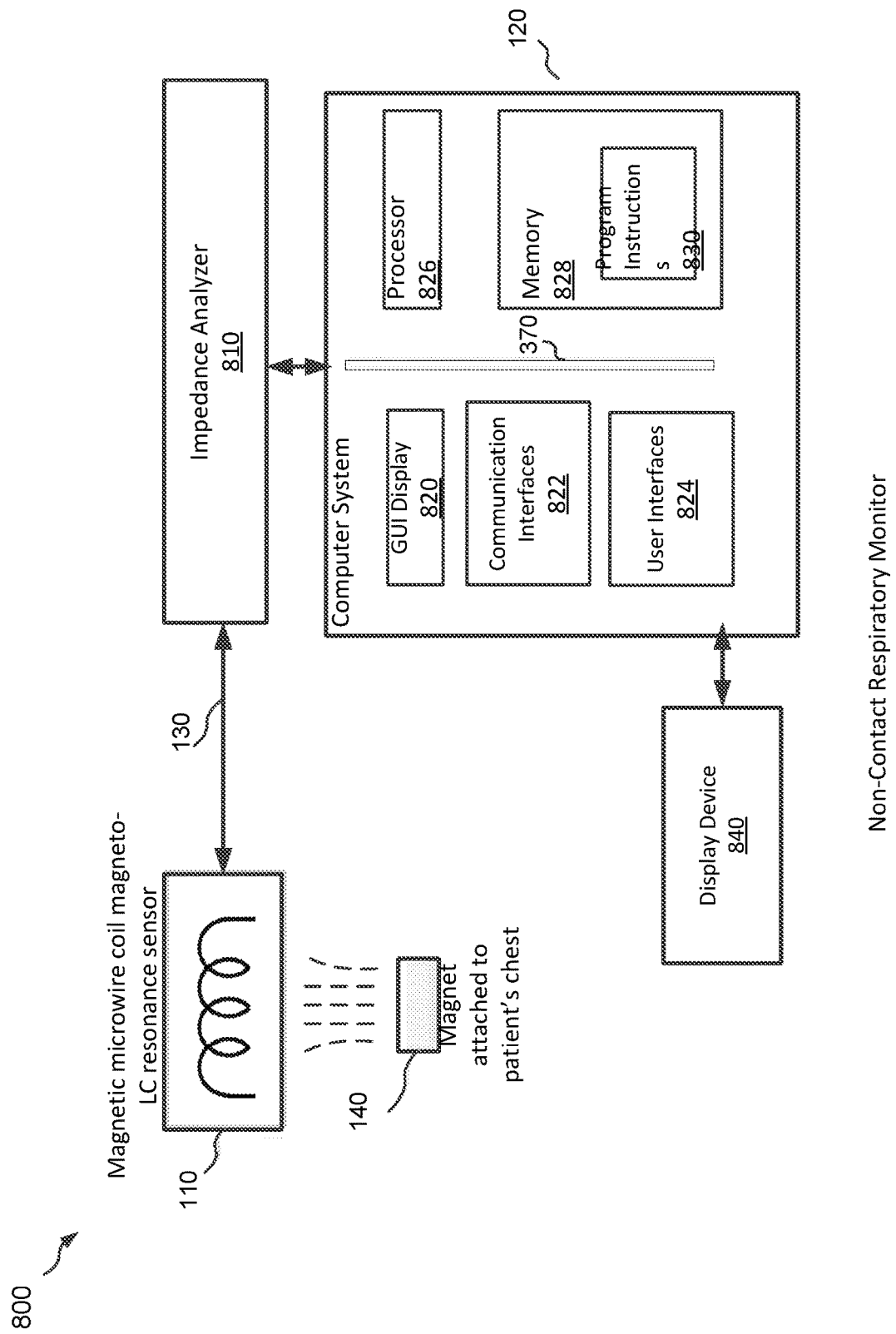
FIG. 8 is a block diagram of a non-contact respiratory sensor comprising a magnetic microwire coil (MMC) magneto-LC resonance sensor.

FIG. 8 is a block diagram of a non-contact respiratory sensor comprising a magnetic microwire coil (MMC) magneto-LC resonance sensor system. Referring to FIG. 8, a non-contact respiratory monitor system includes the MMC 110 sensor, the magnet 140, the communication link 130, an impedance analyzer 810, the computer system 120 and a display 840.

The MMC 110 may comprise a magnetic microwire coil magneto-LC resonance sensor wound from a Co-rich melt-extracted amorphous microwire. In some embodiments, the MMC 110 may be constructed from a high quality melt-extracted amorphous microwire with nominal composition $Co_{69.25}Fe_{4.25}Si_{13}B_{12.5}Nb_1$. The diameter of the microwire may vary, for example, from approximately 20 to 100 μm. The number of turns may vary, for example, from 5-20 turns. The length of the MMC 110 may vary, for example, from 3 to 15 mm. In one exemplary embodiment, the MMC 110 may have 10 turns, be 7.0 mm in length, have a 3 mm internal diameter, and be wound around a quartz tube. In other exemplary embodiments, the magnetic coil may include 5-20 turns, have a length of 5-10 mm, have an internal diameter of 2-5 mm, and may be wound around a quartz or plastic tube, for example. However, the composition of the coil, the composition of the core, the length of the coil, the diameter of the coil, and the number of windings in the MMC 110 may vary according to a design of the MMC sensor system.

The MMC 110 may be oriented, relative to the magnet 140, such that magnetic field lines emanating from the magnet 140 are parallel to a cross-section of the MMC coil, thus, parallel to the sensor coil winding direction.

The distance between the magnet 140 and the MMC 110 may be determined by the stray field of the magnet 140. For example, the average distance between the MMC 110 and the permanent magnet 140 may be between 3.0 cm and 15 cm depending on the operating frequency and the field strength of the magnet 140. The MMC 110 may be positioned a distance from the magnet such that a change in the distance of the magnet 140 from the MMC 110 causes a change of impedance in the MMC 110, which is detected in the MMC 110 sensor. In this regard, when the magnet is attached to a patient's chest, up and down motion of the patient's chest during breathing causes the magnetic field of the magnet to modify the inductance of the coil sensor.

The ends of the MMC 110 may be connected to transmission lines in the communication link 130. The communication link 130 may comprise, for example, a coaxial cable that is connected to terminals in the impedance analyzer 810.

The impedance analyzer 810 may be coupled to the MMC 110 via an RF transmission line 130 and may be coupled to the computer system 120 via a wireline or wireless link for communication of respiratory monitoring information detected by the MMC 110. The impedance analyzer 810 may supply an RF alternating voltage or current to the MMC 110 and may measure changes in impedance of the MMC 110 when return signals are modulated by the change in impedance of the MMC 110 that is generated by motion of the magnet 140 relative to the MMC 110. For example, the motion of the magnet 140 being caused by breathing of a subject attached to the magnet 140.

In operation, a subject's breathing may be monitored by the MMC 110 sensor. The magnet 140 may be attached or placed on a subject's body in a magnetically coupling position relative to the MMC 110, as described above. One or more of the subject's frequency of breathing, breathing patterns, and depth of breathing may be detected by variations of impedance in the MMC 110 caused by respiratory motion of the subjects body and the corresponding motion of the magnet 140 relative to the MMC 110. The MMC 110 may generate an output signal that varies as the change of impedance in the MMC 110, which may be transmitted to the impedance analyzer 810. The impedance analyzer 810 may analyze the MMC 110 output signal and forward respiratory monitoring information to the computer system 120 for display of respiratory function of the subject in the display device 840.

The computer system 120 may be configured to control and receive respiratory monitoring information from the impedance analyzer 810, and generate a display of the respiratory monitoring information to the display device 840. In one embodiment, the program instructions 830 may provide control signals to the impedance analyzer 310 to control the characteristics of alternating voltages or current that is supplied by the impedance analyzer 810 to the MMC 110. The impedance analyzer 810 may determine changes in impedance of the MMC 110 based on changes in the return current flow from the MMC 110, and provide respiratory monitoring information to the computer system 120. The respiratory monitoring information is based on impedance changes detected by the MMC 110 and processed by the impedance analyzer 810. The computer system program instructions 830 may process the respiratory monitoring information. The GUI display engine 820 may generate a graphical user interface (GUI) display based on the respiratory monitoring information and send the GUI display to the display device 840 for viewing by a user. The system 800 may generate and display the respiratory monitoring information in real-time while the magnet 140 is attached to the body of a patient and breathing motions of the patient vary the distance of the magnet 140 to the MMC 110. Although the impedance analyzer 810, the computer system 120 and the display device 840 are shown as separate devices in FIG. 8, the system 800 is not limited in this regard, and the entire system 800 or any combination of sub-systems of the system 800 may be combined in one device or separated in any suitable number of separate devices.

The computer processing system 120 may be any of various types of devices, including, but not limited to, a personal computer system, desktop computer, laptop, notebook, or netbook computer, mainframe computer system, handheld computer, mobile telephone, workstation, network computer, a camera, a set top box, a mobile device, a consumer device, application server, storage device, a peripheral device such as a switch, modem, router, or another type of computing or electronic device.

In the illustrated embodiment, computer system 120 includes one or more processors 826 coupled to a system memory 828 via an input/output (I/O) interface 370. Computer system 120 further includes a network interface 822 coupled to I/O interface 370, and one or more input/output devices, such as the impedance analyzer 810, cursor control device, keyboard, and display(s) 840. In some embodiments, it is contemplated that embodiments may be implemented using a single instance of computer system 120, while in other embodiments multiple such systems, or multiple nodes making up computer system 120, may be configured to host different portions or instances of embodiments. For example, in one embodiment some elements may be implemented via one or more nodes of computer system 120 that are distinct from those nodes implementing other elements.

In various embodiments, computer system 120 may be a uniprocessor system including one processor 826, or a multiprocessor system including several processors 826 (e.g., two, four, eight, or another suitable number). Processors 826 may be any suitable processor capable of executing instructions. For example, in various embodiments, processors 826 may implement any of a variety of instruction set architectures (ISAs), such as the x86, PowerPC, SPARC, or MIPS ISAs, or any other suitable ISA. In multiprocessor systems, each of processors 826 may commonly, but not necessarily, implement the same ISA.

In some embodiments, at least one processor 826 may be a graphics processing unit. A graphics processing unit or GPU may be considered a dedicated graphics-rendering device for a personal computer, portable phone, laptop, tablet, workstation, or other computing or electronic device. Modern GPUs may be very efficient at manipulating and displaying computer graphics, and their highly parallel structure may make them more effective than typical CPUs for a range of complex graphical algorithms. For example, a graphics processor may implement a number of graphics primitive operations in a way that makes executing them much faster than drawing directly to the screen with a host central processing unit (CPU). In various embodiments, the image processing methods disclosed herein may, at least in part, be implemented by program instructions configured for execution on one of, or parallel execution on two or more of, such GPUs. The GPU(s) may implement one or more application programmer interfaces (APIs) that permit programmers to invoke the functionality of the GPU(s). Suitable GPUs may be commercially available from vendors such as NVIDIA Corporation, ATI Technologies (AMD), and others.

System memory 828 may be configured to store program instructions 830 and/or data accessible by processor 826. In various embodiments, system memory 828 may be implemented using any suitable memory technology, such as static random access memory (SRAM), synchronous dynamic RAM (SDRAM), nonvolatile/Flash-type memory, or any other type of memory. In the illustrated embodiment, program instructions and data implementing desired functions, such as those described above for various embodiments, are shown stored within system memory 828 as program instructions 830. In other embodiments, program instructions and/or data may be received, sent or stored upon different types of computer-accessible media or on similar media separate from system memory 828 or computer system 120. Moreover, in some embodiments, a database that is accessible via a network may store, among other things, MMC 110 sensor respiratory monitoring data received from the impedance analyzer. Generally speaking, a computer-accessible medium may include storage media or memory media such as magnetic or optical media, e.g., disk or CD/DVD-ROM coupled to computer system 120 via an I/O interface 370. Program instructions and data stored via a computer-accessible medium may be transmitted by transmission media or signals such as electrical, electromagnetic, or digital signals, which may be conveyed via a communication medium such as a network and/or a wireless link, such as may be implemented via network communication interfaces 820.

In one embodiment, I/O interface 370 may be configured to coordinate I/O traffic between processor 826, system memory 828, and any peripheral devices, including for example, the network interface 822 or other peripheral interfaces, such as the impedance analyzer 810 and display device 840. In some embodiments, I/O interface 370 may perform any necessary protocol, timing or other data transformations to convert data signals from one component (e.g., system memory 828 or impedance analyzer 810) into a format suitable for use by another component (e.g., processor 826). In some embodiments, I/O interface 370 may include support for devices attached through various types of peripheral buses, such as a variant of the Peripheral Component Interconnect (PCI) bus standard or the Universal Serial Bus (USB) standard, for example. In some embodiments, the function of I/O interface 370 may be split into two or more separate components, such as a north bridge and a south bridge, for example. In addition, in some embodiments some or all of the functionality of I/O interface 370, such as an interface to system memory 828, may be incorporated directly into processor 826.

Network interface 822 may be configured to allow data to be exchanged between computer system 120 and other devices attached to a network, such as other computer systems, a database, or between nodes of computer system 120. In various embodiments, network interface 822 may support communication via wired or wireless general data networks, such as any suitable type of Ethernet network, for example; via telecommunications/telephony networks such as analog voice networks or digital fiber communications networks; via storage area networks such as Fiber Channel SANs, or via any other suitable type of network and/or protocol. In some embodiments, the impedance analyzer 810 may be communicatively coupled to the computer system 120 via a network and the network communication interface 822.

Input/output devices connected to the computer system 120 may, in some embodiments, include one or more of the impedance analyzer 810, display terminals 840, keyboards, keypads, touchpads, scanning devices, voice or optical recognition devices, or any other devices suitable for entering or retrieving data by one or more computer system 120. Multiple input/output devices may be present in computer system 120 or may be distributed on various nodes of computer system 120. In some embodiments, similar input/output devices may be separate from computer system 120 and may interact with one or more nodes of computer system 120 through a wired or wireless connection, such as over network interface 822.

Those skilled in the art will also appreciate that, while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 120 may be transmitted to computer system 120 via transmission media or signals such as electrical, electromagnetic, or digital signals, conveyed via a communication medium such as a network and/or a wireless link. Various embodiments may further include receiving, sending or storing instructions and/or data implemented in accordance with the foregoing description upon a computer-accessible medium. Accordingly, the present embodiments may be practiced with other computer system configurations.

Various embodiments may further include receiving, sending or storing instructions and/or data implemented in accordance with the foregoing description upon a computer-accessible medium. Generally speaking, a computer-accessible medium may include storage media or memory media such as magnetic or optical media, e.g., disk or DVD/CD-ROM, volatile or non-volatile media such as RAM (e.g. SDRAM, DDR, RDRAM, SRAM, etc.), ROM, etc., as well as transmission media or signals such as electrical, electromagnetic, or digital signals, conveyed via a communication medium such as network and/or a wireless link.

The various methods as illustrated in the Figures and described herein represent example embodiments of methods. The methods may be implemented in software, hardware, or a combination thereof. The order of method may be changed, and various elements may be added, reordered, combined, omitted, modified, etc.

Various modifications and changes may be made to the system 800 as would be obvious to a person skilled in the art having the benefit of this disclosure. It is intended that the present embodiments embrace all such modifications and changes and, accordingly, the above description to be regarded in an illustrative rather than a restrictive sense.

Thus, the embodiments provide, among other things, systems and methods for using magneto-LC resonance technology for real-time non-contact respiratory motion monitoring. Various features and advantages are set forth in the following claims.

What is claimed is:

1. A non-contact respiratory monitoring system, the system comprising:
   a permanent magnet; and
   a sensor, the sensor including a coil made of a cobalt-rich magnetic microwire, the magnetic microwire sensor coil configured to detect motion of the permanent magnet relative to the magnetic sensor coil, wherein the magnetic microwire sensor coil is:
      oriented such that field lines emanating from the permanent magnet are parallel to a cross-sectional area of the magnetic microwire sensor coil and the magnetic microwire sensor coil winding direction, and
      positioned a distance from the permanent magnet such that the magnetic microwire sensor coil is magnetically coupled to the magnet, wherein a change in the distance of the permanent magnet from the magnetic microwire sensor coil causes a change of impedance in the magnetic microwire sensor coil,
   wherein an alternating voltage across the magnetic microwire sensor coil is modified by a change in impedance of the magnetic microwire sensor coil caused by the change in the distance of the permanent magnet from the magnetic microwire sensor coil, and wherein the cobalt-rich magnetic microwire has a diameter ranging from 20 μm to 100 μm, and the coil includes 5 to 20 turns, has a length ranging from 3 mm to 15 mm, and has an internal diameter ranging from 2 mm to 5 mm.

2. The system of claim 1 further comprising:

an impedance analyzer coupled to the ends of the magnetic microwire sensor coil, wherein the impedance analyzer measures the change in impedance of the magnetic microwire sensor coil caused by the change in the distance of the permanent magnet from the magnetic microwire sensor coil.

3. The system of claim 2 further comprising:

a computer system communicatively coupled to the impedance analyzer, the computer system comprising an electronic processor coupled to a memory storing instructions that when executed by the electronic processor cause the electronic processor to:

communicate operation commands to the impedance analyzer for generation of a carrier signal to the magnetic microwire sensor coil; and receive respiratory monitoring information from the impedance analyzer, the respiratory monitoring information based on a return signal from the magnetic microwire sensor coil that indicates the change in impedance of the magnetic microwire sensor coil caused by the change in the distance of the permanent magnet from the magnetic microwire sensor coil.

4. The system of claim 3 further comprising:

a display device, wherein the electronic processor sends the respiratory monitoring information to a display device to display the respiratory monitoring information based on the return signal from the magnetic microwire sensor coil that indicates the change in impedance of the magnetic microwire sensor coil caused by the change in the distance of the permanent magnet from the magnetic microwire sensor coil.

5. The system of claim 1, wherein the permanent magnet is attached to a patient's chest or abdomen for monitoring the patient's respiratory motion.

6. The system of claim 1, wherein the respiratory monitoring information comprises one or more of frequency of breathing, a breathing pattern, and a depth of breathing that is detected by the changes in impedance of the magnetic microwire sensor coil.

7. The system of claim 1, wherein the magnetic microwire sensor coil is configured to detect small magnetic fields in a range of about 0.01 Oe to about 20 Oe.

* * * * *